United States Patent [19]

Garcia

[11] Patent Number: 5,792,132
[45] Date of Patent: Aug. 11, 1998

[54] INCONTINENCE DIAPER SYSTEM

[76] Inventor: Lucia Marta Garcia, 4655 Palmane Ave., #111, Hialeah, Fla. 33012

[21] Appl. No.: 791,658

[22] Filed: Jan. 30, 1997

[51] Int. Cl.$^6$ .............................. A61F 13/15; A61F 5/44
[52] U.S. Cl. ............... 604/385.1; 604/349; 604/329; 604/353
[58] Field of Search ................. 604/329–331, 604/349–353, 385.1

[56] References Cited

U.S. PATENT DOCUMENTS

| | | | |
|---|---|---|---|
| 5,053,027 | 10/1991 | Manfredi | 604/331 |
| 5,295,983 | 3/1994 | Kubo | 604/329 |
| 5,462,539 | 10/1995 | Herman et al. | 604/348 |
| 5,645,541 | 7/1997 | Bonser | 604/353 |

*Primary Examiner*—Robert A. Clarke

[57] ABSTRACT

An incontinence diaper system for providing an incontinence diaper with a drainage system to reduce urine excrement retention with the incontinence diaper. The incontinence diaper system includes a diaper having a drain aperture, an interior liner juxtaposed to the diaper having a funnel aperture into one side, a drain funnel secured within the funnel aperture to collect the urine absorbed by the interior liner, a tubing coupled to the drain funnel opposite of the funnel aperture, and a reservoir coupled to the tubing opposite of the drain funnel to store the collected urine which flows through the tubing. For males, an elongated tapering tube having a bulbous enlarged end for coupling to the penis.

6 Claims, 3 Drawing Sheets

5,792,132

INCONTINENCE DIAPER SYSTEM

BACKGROUND OF THE INVENTION

1. Field of the Invention

The present invention relates to Diaper Devices and more particularly pertains to a new Incontinence Diaper System for providing an incontinence diaper with a drainage system to reduce urine excrement retention with the incontinence diaper.

2. Description of the Prior Art

The use of Diaper Devices is known in the prior art. More specifically, Diaper Devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art Diaper Devices include U.S. Pat. No. 4,886,508; U.S. Pat. No. 4,410,327; U.S. Pat. No. 4,678,464; U.S. Pat. No. 4,559,051; U.S. Design Pat. No. 302,854 and U.S. Pat. No. 4,718,901.

While these devices fulfill their respective, particular objectives and requirements, the aforementioned patents do not disclose a new Incontinence Diaper System. The inventive device includes a diaper having a drain aperture, an interior liner juxtaposed to the diaper having a funnel aperture into one side, a drain funnel secured within the funnel aperture to collect the urine absorbed by the interior liner, a tubing coupled to the drain funnel opposite of the funnel aperture, and a reservoir coupled to the tubing opposite of the drain funnel to store the collected urine which flows through the tubing. For males, an elongated tapering tube couples to the penis at one end and couples to the tubing.

In these respects, the Incontinence Diaper System according to the present invention substantially departs from the conventional concepts and designs of the prior art, and in so doing provides an apparatus primarily developed for the purpose of providing an incontinence diaper with a drainage system to reduce urine excrement retention with the incontinence diaper.

SUMMARY OF THE INVENTION

In view of the foregoing disadvantages inherent in the known types of Diaper Devices now present in the prior art, the present invention provides a new Incontinence Diaper System construction wherein the same can be utilized for providing an incontinence diaper with a drainage system to reduce urine excrement retention with the incontinence diaper.

The general purpose of the present invention, which will be described subsequently in greater detail, is to provide a new Incontinence Diaper System apparatus and method which has many of the advantages of the Diaper Devices mentioned heretofore and many novel features that result in a new Incontinence Diaper System which is not anticipated, rendered obvious, suggested, or even implied by any of the prior art Diaper Devices, either alone or in any combination thereof.

To attain this, the present invention generally comprises a diaper having a drain aperture, an interior liner juxtaposed to the diaper having a funnel aperture into one side, a drain funnel secured within the funnel aperture to collect the urine absorbed by the interior liner, a tubing coupled to the drain funnel opposite of the funnel aperture, and a reservoir coupled to the tubing opposite of the drain funnel to store the collected urine which flows through the tubing. For males, an elongated tapering tube couples to the penis at one end and couples to the tubing.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Incontinence Diaper System apparatus and method which has many of the advantages of the Diaper Devices mentioned heretofore and many novel features that result in a new Incontinence Diaper System which is not anticipated, rendered obvious, suggested, or even implied by any of the prior art Diaper Devices, either alone or in any combination thereof.

It is another object of the present invention to provide a new Incontinence Diaper System which may be easily and efficiently manufactured and marketed.

It is a further object of the present invention to provide a new Incontinence Diaper System which is of a durable and reliable construction.

An even further object of the present invention is to provide a new Incontinence Diaper System which is susceptible of a low cost of manufacture with regard to both materials and labor, and which accordingly is then susceptible of low prices of sale to the consuming public, thereby making such Incontinence Diaper System economically available to the buying public.

Still yet another object of the present invention is to provide a new Incontinence Diaper System which provides in the apparatuses and methods of the prior art some of the advantages thereof, while simultaneously overcoming some of the disadvantages normally associated therewith.

Still another object of the present invention is to provide a new Incontinence Diaper System for providing an incontinence diaper with a drainage system to reduce urine excrement retention with the incontinence diaper.

Yet another object of the present invention is to provide a new Incontinence Diaper System which includes a diaper having a drain aperture, an interior liner juxtaposed to the diaper having a funnel aperture into one side, a drain funnel secured within the funnel aperture to collect the urine absorbed by the interior liner, a tubing coupled to the drain funnel opposite of the funnel aperture, and a reservoir coupled to the tubing opposite of the drain funnel to store the collected urine which flows through the tubing. For males, an elongated tapering tube couples to the penis at one end and couples to the tubing.

Still yet another object of the present invention is to provide a new Incontinence Diaper System that reduces the number of changes of diapers required for a bed ridden person.

Even still another object of the present invention is to provide a new Incontinence Diaper System that has a movable mesh which avoids obstruction of the urine exit because of the bowels evacuations.

Another object of the present invention is to provide a new Incontinence Diaper System that will keep bed ridden patients dry during day or night.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
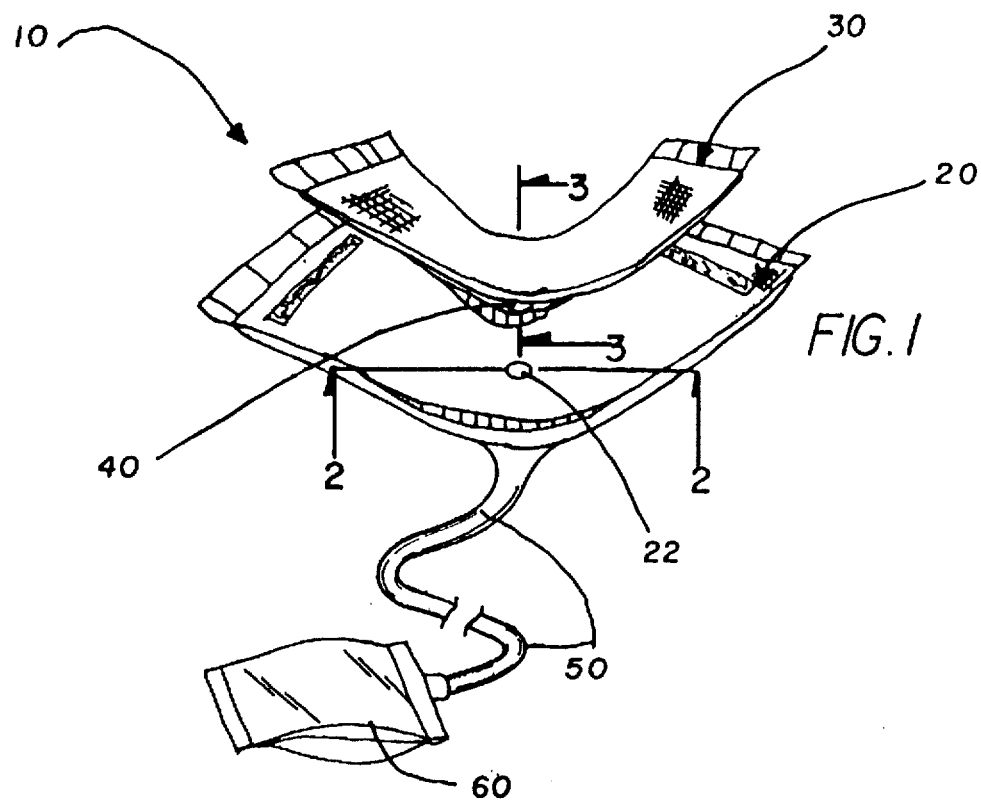
FIG. 1 is an upper side perspective view of a new Incontinence Diaper System according to the present invention.

With reference now to the drawings, and in particular to FIGS. 1 through 6 thereof, a new Incontinence Diaper System embodying the principles and concepts of the present invention and generally designated by the reference numeral 10 will be described.

More specifically, it will be noted that the Incontinence Diaper System 10 comprises a diaper 20, an interior liner, a drain funnel, a length of tubing and a reservoir. A drain aperture 22 projects concentrically through the diaper 20. The interior liner 30 is juxtaposed to an interior surface of the diaper 20, where the interior liner 30 captures urine excrement while excluding bowels evacuations, the interior liner 30 has funnel aperture 38 into the side juxtaposed to the diaper 20. The funnel aperture 38 aligns with the drain aperture 22 as shown in FIG. 1 of the drawings. The drain funnel 40 mates within the funnel aperture 38, where the drain funnel 40 receives the urine excrement. The length of tubing 50 mates with the drain funnel 40 and projects through the drain aperture 22, thereby forming an exit for the urine excrement.

Figure 2:
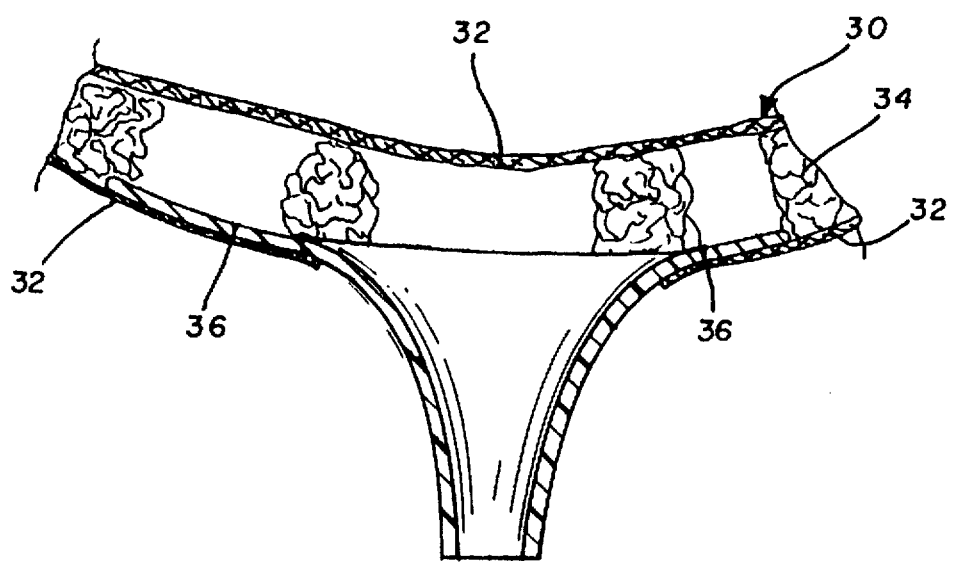
FIG. 2 is a cross sectional view taken along line 2—2 of FIG. 1.
Figure 3:
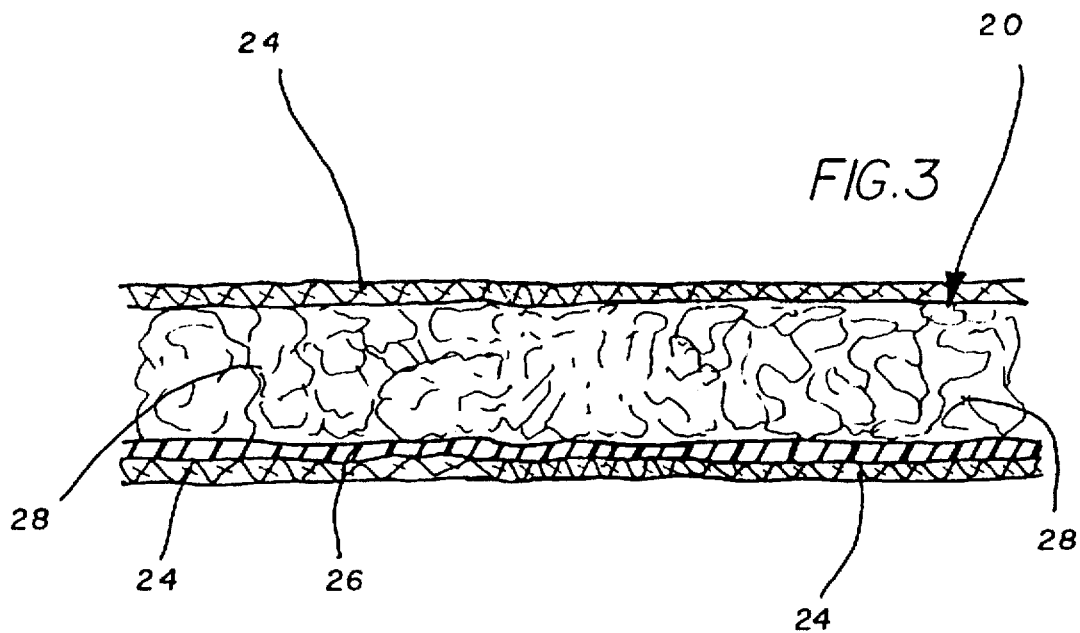
FIG. 3 is a cross sectional view taken along line 3—3 of FIG. 1.
Figure 5:
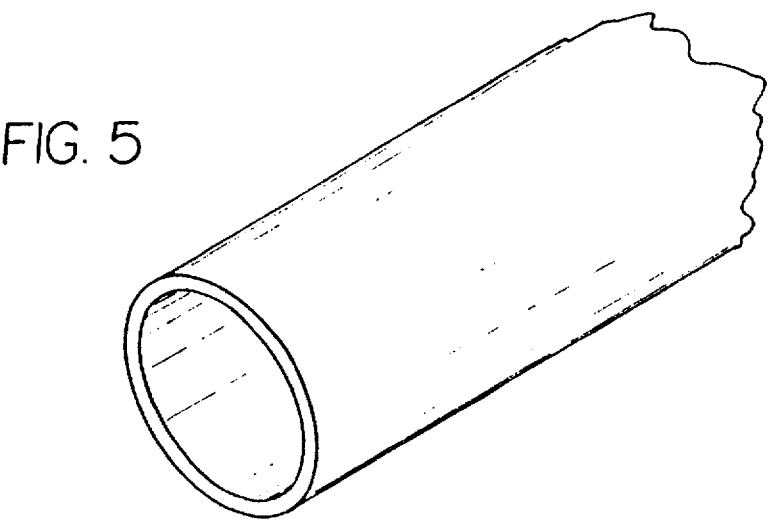
FIG. 5 is a cross sectional view taken along line 5—5 of FIG. 4.

As best illustrated in FIG. 1, it can be shown that a reservoir 60 is coupled to the tubing 50 opposite of the drain funnel 40, thereby containing and storing the urine excrement. The interior liner 30 has a permeable mesh encasement 32 surrounding a semi-absorbent filling 34. A resilient swaged impermeable member 36 is juxtaposed to the interior bottom surface of the permeable mesh encasement 32 adjacent to the drain funnel 40 as shown in FIG. 2 of the drawings. As shown in FIG. 5, the tubing 50 has a length of tape 52 around the outer perimeter portion that engages the drain aperture 22, thereby retaining the tubing 50 firmly positioned.

Figure 4:
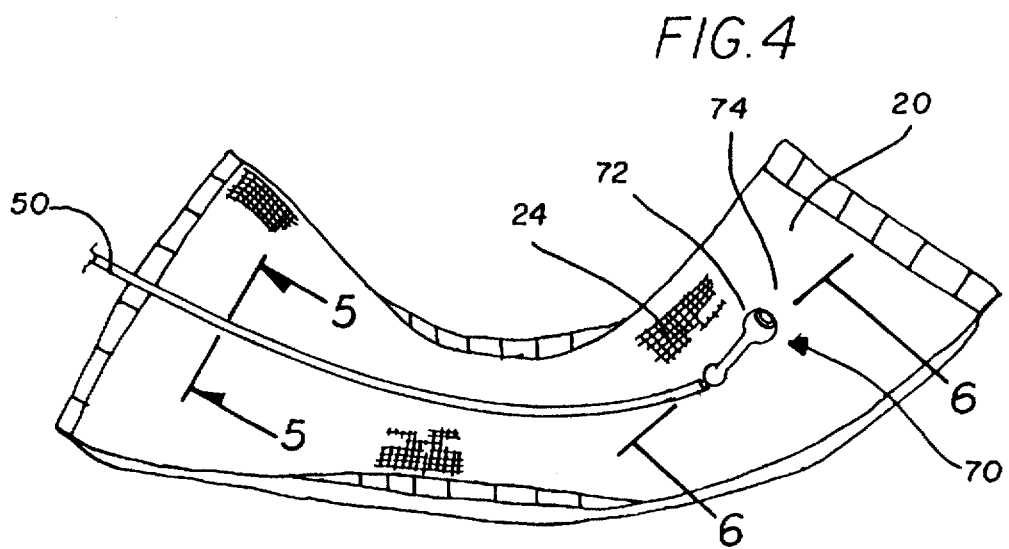
FIG. 4 is an upper side perspective view of an alternative embodiment.
Figure 6:
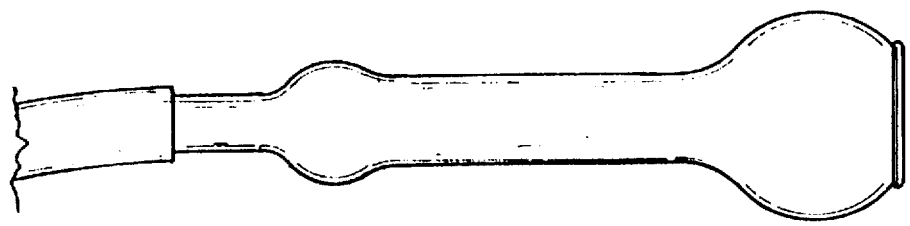
FIG. 6 is a cross sectional view taken along line 6—6 of FIG. 4.

As shown in FIGS. 4 and 6 of the drawings, an alternative embodiment has a penis coupler 70 comprising an elongated tapering tube 72 having an enlarged end 76 and a narrow end 78. A cincture 74 surrounds the edge of the enlarged end 76. The enlarged end 76 removably couples to an unnumbered penis. A length of tubing 50 mates with the narrow end 78, thereby forming an exit for the urine excrement. The reservoir 60 is coupled to the tubing 50 opposite of the elongated tapering tube 72, thereby containing and storing the urine excrement.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An incontinence diaper system comprising:

a diaper;

said diaper including a drain aperture projecting concentrically through;

an interior liner juxtaposed to an interior surface of said diaper, where said interior liner captures urine excrement while excluding bowels evacuations;

said interior liner including a funnel aperture into the side juxtaposed to said diaper, where said funnel aperture aligns with said drain aperture;

a drain funnel mating within said funnel aperture, where said drain funnel receives said urine excrement; and a length of tubing mating with said drain funnel and projecting through said drain aperture, thereby forming an exit for said urine excrement.

2. The incontinence diaper system of claim 1, wherein a reservoir is coupled to said tubing opposite of said drain funnel, thereby containing and storing said urine excrement.

3. The incontinence diaper system of claim 2, wherein said interior liner comprises:

a permeable mesh encasement surrounding a semi-absorbent filling; and a resilient swaged impermeable member juxtaposed to the interior bottom surface of said permeable mesh encasement adjacent to said drain funnel.

4. The incontinence diaper system of claim 3, wherein said tubing including a length of tape around the outer perimeter portion that engages said drain aperture, thereby retaining said tubing firmly in place.

5. An incontinence diaper system comprising:

a diaper;

a penis coupler extending from said diaper, said penis coupler including an elongated tapering tube having a bulbous enlarged end and a narrow end with a cincture surrounding an edge of said bulbous enlarged end, where said enlarged end removably couples to a penis; and a length of tubing mating with said narrow end, thereby forming an exit for said urine excrement.

6. The incontinence diaper system of claim 5, wherein a reservoir is coupled to said tubing opposite of said narrow end, thereby containing and storing said urine excrement.

* * * * *